United States Patent
Schroeder et al.

(10) Patent No.: US 10,722,440 B2
(45) Date of Patent: Jul. 28, 2020

(54) HAIR CLEANING PRODUCT

(71) Applicant: Henkel AG & Co. KGaA, Duesseldorf (DE)

(72) Inventors: Thomas Schroeder, Hamburg (DE);
Edith von Aspern, Hanstedt (DE);
Dirk Hentrich, Hamburg (DE);
Manuela Mette, Kleinfeld (DE);
Soeren Scheele, Pinneberg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 15 days.

(21) Appl. No.: 16/037,760

(22) Filed: Jul. 17, 2018

(65) Prior Publication Data
US 2019/0021971 A1 Jan. 24, 2019

(30) Foreign Application Priority Data

Jul. 19, 2017 (DE) .......................... 10 2017 212 401

(51) Int. Cl.
*A61K 8/00* (2006.01)
*A61K 8/46* (2006.01)
*A61K 8/92* (2006.01)
*A61K 8/31* (2006.01)
*A61K 8/44* (2006.01)
*A61Q 5/02* (2006.01)

(52) U.S. Cl.
CPC ................ *A61K 8/463* (2013.01); *A61K 8/31* (2013.01); *A61K 8/442* (2013.01); *A61K 8/466* (2013.01); *A61K 8/922* (2013.01); *A61Q 5/02* (2013.01); *A61K 2800/596* (2013.01); *A61K 2800/5922* (2013.01)

(58) Field of Classification Search
None
See application file for complete search history.

(56) References Cited

U.S. PATENT DOCUMENTS

| 6,274,128 B1 * | 8/2001 | Bergmann | A61K 8/19 424/400 |
| 8,722,029 B2 | 5/2014 | Desenne et al. | |
| 8,956,598 B2 * | 2/2015 | Jackwerth | A61K 8/31 424/65 |
| 9,072,915 B2 | 7/2015 | Desenne et al. | |
| 9,566,220 B2 | 2/2017 | Desenne et al. | |
| 9,827,178 B2 | 11/2017 | Desenne et al. | |
| 2008/0028772 A1 | 2/2008 | Lee et al. | |
| 2017/0112739 A1 * | 4/2017 | Molenda | A61Q 5/12 |
| 2017/0333734 A1 * | 11/2017 | Mauer | A61K 8/922 |

FOREIGN PATENT DOCUMENTS

| EP | 2338466 A1 | 6/2011 |
| EP | 2338467 A1 | 6/2011 |
| EP | 2338468 A1 | 6/2011 |
| EP | 2338469 A1 | 6/2011 |
| WO | 2008155059 A2 | 12/2008 |
| WO | 2010115973 A1 | 10/2010 |

* cited by examiner

*Primary Examiner* — Necholus Ogden, Jr.
(74) *Attorney, Agent, or Firm* — Lorenz & Kopf, LLP

(57) ABSTRACT

Hair cleansing products containing anionic surfactants, amphoteric surfactants, a mixture of specific linear alkanes and a non-polymeric structuring agent, suitable for the cleansing and nourishing of hair, in particular in order to improve
the wet and dry combability,
the detangling capability,
the feel, and
the shine of hair.

8 Claims, No Drawings

HAIR CLEANING PRODUCT

CROSS-REFERENCE TO RELATED APPLICATION

This application claims priority to German Patent Application No. 10 2017 212 401.6, filed Jul. 19, 2017, which is incorporated herein by reference in its entirety.

TECHNICAL FIELD

The application describes hair cleansing products based on an active substance combination of anionic and amphoteric surfactants, specific linear alkanes, and non-polymeric structuring agents, and also the use of these products to cleanse and nourish keratin fibres.

BACKGROUND

Human hair and the scalp can be cleansed using cosmetic cleansing products (hair shampoos), and said cleansing products can also be used to remove sebum, styling product residues and other soiling from the hair and scalp.

Due to the surfactants (mostly anionic) usually contained in cosmetic hair cleansing products, hair cleansing is always accompanied by a removal of lipids and proteins from the hair or scalp, whereby, in particular in the event of frequent cleansing, the hair structure can become damaged and/or the scalp can become dry. Damage to the hair structure or the hair fibres, in particular split ends and/or breakage, can also be intensified by ambient conditions (for example intense solar radiation), mechanical stresses (such as combing whilst blow-drying), and by chemical influences (such as dyeing, shaping or smoothing the hair).

In order to prevent and/or reduce hair damage, oil-based care substances, usually silicones, were often added to hair shampoos in the past.

The use of silicones in hair cleansing products, however, is the subject of controversy and has disadvantages, because silicones, by wetting the hair surface, reduce the penetration of active substances and auxiliaries into the hair and make it more difficult to style the hair.

In addition, for reasons of sustainability, it is sought to use the maximum proportion possible of biologically degradable active substances in cosmetic products. The provision of low-silicone or silicone-free stable, nourishing hair cleansing products is therefore a relevant task in the field of hair cosmetics.

In the prior art, the group of linear paraffins has been discussed as one of many active substance classes suitable for substitution of silicones. For example, patent application WO 2010/115973A1 (to Biosynthis) describes cosmetic compositions which contain mixtures of linear $C_8$-$C_{12}$ alkanes and $C_{14}$-$C_{24}$ alkanes besides further constituents. These compositions, however, also have a series of disadvantages and, in spite of previous achievements, there is still a need for low-silicone or silicone-free hair cleansing products based on volatile "light emollients".

BRIEF SUMMARY

This disclosure provides a hair cleansing product that includes a) at least one anionic surfactant, b) at least one amphoteric surfactant, c) at least one linear alkane selected from C9, C10, C11 and C12 alkanes and mixtures of these alkanes, d) at least one linear alkane selected from C15, C16, C17, C18, C19, C20, C21, C22 and C23 alkanes and mixtures of these alkanes, and e) at least one non-polymeric structuring agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now been found that, by way of the combination of anionic and amphoteric surfactants with specific linear alkanes and non-polymeric structuring agents, hair cleansing products that have excellent cleansing and nourishing effect can be obtained.

These viscosity-stable and storage-stable products cause the hair treated therewith to have an improved feel and shine and also excellent detangling properties and combability properties.

A first subject matter of this application is a hair cleansing product containing
a) at least one anionic surfactant,
b) at least one amphoteric surfactant,
c) at least one linear alkane selected from $C_9$, $C_{10}$, $C_{11}$ and $C_{12}$ alkanes and mixtures of these alkanes,
d) at least one linear alkane selected from $C_{15}$, $C_{16}$, $C_{17}$, $C_{18}$, $C_{19}$, $C_{20}$, $C_{21}$, $C_{22}$ and $C_{23}$ alkanes and mixtures of these alkanes, and
e) at least one non-polymeric structuring agent.

Particularly preferred hair cleansing products contain, in accordance with a first preferred embodiment, from about 3.00 to about 30.00% by weight of at least one anionic surfactant a),
   from about 1.00 to about 20.00% by weight of at least one amphoteric surfactant b),
   from about 0.10 to about 20.00% by weight of at least one linear alkane c),
   from about 0.10 to about 20.00% by weight of at least one linear alkane d) and
   from about 0.01 to about 5.00% by weight of at least one non-polymeric structuring agent e).

The hair cleansing products as contemplated herein contain the active substances a) to e) preferably in a cosmetically acceptable carrier. This is preferably understood within the scope of the present disclosure to mean an aqueous or aqueous-alcoholic carrier.

The cosmetic carrier preferably contains at least about 50% by weight, more preferably at least about 60% by weight, particularly preferably at least about 70% by weight, and in particular preferably at least about 75% by weight of water.

Furthermore, the cosmetic carrier can contain from about 0.01 to about 40% by weight, preferably from about 0.05 to about 30% by weight, and in particular from about 0.1 to about 20% by weight of at least one alcohol.

Suitable alcohols are, for example, ethanol, ethyldiglycol, 1-propanol, 2-propanol, isopropanol, 1,2-propylene glycol, glycerol, diglycerol, triglycerol, 1-butanol, 2-butanol, 1,2-butanediol, 1,3-butandeiol, 1-pentanol, 2-pentanol, 1,2-pentanediol, 1,5-pentanediol, 1, hexanol, 2-hexanol, 1,2-hexanediol, 1,6-hexanediol, polyethylene glycols, sorbitol, sorbitan, benzyl alcohol, phenoxyethanol or mixtures of these alcohols.

The water-soluble alcohols are particularly preferred.

Ethanol, 1,2-propylene glycol, glycerol, benzyl alcohol and/or phenoxyethanol and mixtures of these alcohols are preferred in particular.

For very good compatibility of the hair cleansing products as contemplated herein with the skin (scalp) it is advantageous if they have a slightly acidic pH value.

It has been found that the products as contemplated herein have particularly good skin compatibility and gentleness in a pH range of from about 4.0 to about 6.0.

In a preferred embodiment the hair cleansing products as contemplated herein have a pH value in the range of from about 4.0 to about 6.0, more preferably from about 4.5 to about 5.5, and in particular preferably from about 5.0 to about 0.2.

The gentleness and foaming properties of the hair cleansing products as contemplated herein can be increased significantly by careful selection of the surfactant volumes, the surfactant types, and the ratio by weight between anionic surfactants a) and amphoteric surfactants b).

An excess of the at least one anionic surfactant a) to the at least one amphoteric surfactant b) has proven to be particularly preferred for attaining an optimal balance between gentleness and foaming properties of the products as contemplated herein.

In a further preferred embodiment the ratio by weight of the at least one anionic surfactant a) to the at least one amphoteric surfactant b) in the hair cleansing products as contemplated herein is therefore preferably from about 5:1 to about 2:1, particularly preferably from about 4.75:1 to about 2.25:1 and in particular from about 4.5:1 to about 2.5:1.

A total surfactant content of at most about 25% by weight, particularly preferably of at most about 20% by weight, and in particular of at most about 17.5% by weight is also preferred, wherein the specified amounts relate to the total weight of the hair cleansing product.

Suitable anionic surfactant types a) that can be used in the hair cleansing products as contemplated herein include, for example:

linear and branched fatty acids having from 8 to 30 C atoms (soaps), ether carboxylic acids of formula R—O—(CH$_2$—CH$_2$O)$_x$—CH$_2$—COOH, in which R is a linear or branched, saturated or unsaturated alkyl group having from about 8 to about 30 C atoms and x=0 or is from about 1 to about 16, acyl sarcosides having from 8 to 24 C atoms in the acyl group (sarcosinate surfactants), acyl taurides having from 8 to 24 C atoms in der acyl group (taurate surfactants), acyl isethionates having from 8 to 24 C atoms in der acyl group (isethionate surfactants), sulfosuccinic acid mono- and/or -dialkyl esters having from 8 to 24 C atoms in the alkyl group, and sulfosuccinic acid monoalkylpolyoxyethyl esters having from 8 to 24 C atoms in the alkyl group and from 1 to 6 oxyethyl groups (sulfosuccinate surfactants), alpha-olefin sulfonates having from 8 to 24 C atoms (alpha-olefin sulfonate surfactants), alkyl sulfates und/or alkylether sulfate salts of formula R—(OCH$_2$—CH$_2$)$_n$—O—SO$_3$X, in which R is preferably a straight-chain or branched, saturated or unsaturated alkyl group having from 8 to 30 C atoms, x is the number 0 or from 1 to 12 and X means an alkali and/or alkaline earth, ammonium or alkanolamine ion, sulfonates of unsaturated fatty acids having from 8 to 24 C atoms and from 1 to 6 double bonds, esters of tartaric acid and citric acid with alcohols which constitute addition products of approximately 2 to 15 molecules of ethylene oxide and/or propylene oxide with fatty alcohols having from 8 to 22 C atoms, and/or alkyl and/or alkenyl ether phosphates of formula

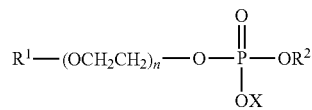

in which R$^1$ preferably stands for an aliphatic hydrocarbon group having from 8 to 30 carbon atoms, R$^2$ stands for hydrogen, a group (CH$_2$CH$_2$O)$_n$R$^1$ or X, n stands for numbers of from about 0 to about 10 and X stands for hydrogen, an alkali or alkaline earth metal, or the group —NR$^3$R$^4$R$^5$R$^6$, with R$^3$ to R$^6$ independently of one another standing for a C$_1$ to C$_4$ hydrocarbon group.

Suitable amphoteric surfactant types b) that can be used in the hair cleansing products as contemplated herein include, for example, one or more compounds of the following formulas (I) to (VII). Therein, the group R stands preferably for a straight-chain or branched, saturated or mono- or polyunsaturated alkyl or alkenyl group having from 7 to 23 carbon atoms (formulas (I) and (II)) or for a straight-chain or branched, saturated or mono- or polyunsaturated alkyl or alkenyl group having from 8 to 24 carbon atoms (formulas (III) to (VII)):

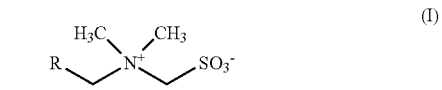
(I)

(II)

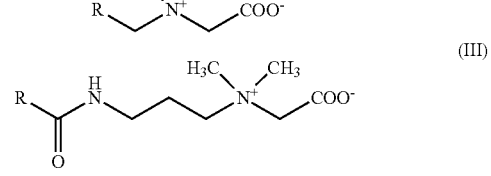
(III)

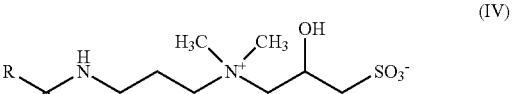
(IV)

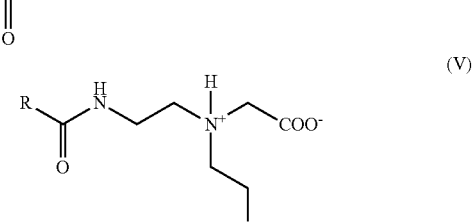
(V)

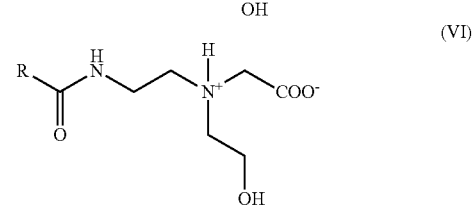
(VI)

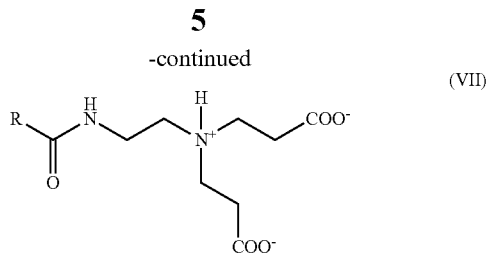

Preferred amphoteric surfactants b) of the aforementioned formulas (I) to (VII) contain, as group R, primarily a straight-chain or branched, saturated, monounsaturated or polyunsaturated alkyl group having from 8 to 20, more preferably from 8 to 18, and in particular having from 8 to 16 C atoms.

Amphoteric surfactants b) in which the group R derives from coconut oil are particularly preferred. The amphoteric surfactants known under the INCI names Sodium Cocoamphoacetate, Disodium Cocoamphodiacetate, Sodium Lauroamphoacetate, Sodium Lauroamphodiacetate, Sodium Cocoamphopropionate, Disodium Cocoamphodipropionate, Coco Betaine, Lauryl Betaine Cocamidopropyl betaine and/or Lauramidopropyl betaine and commercially available from a number of suppliers are very particularly preferred.

Surfactants with the INCI names Cocamidopropyl betaine, Lauramidopropyl betaine, Cocoampho(di)acetate and/or Lauroapho(di)acetate are in particular preferred.

Particularly preferred anionic surfactants a) in the sense of the present disclosure are alkyl(ether) sulfates on account of their excellent foaming properties. These are combined preferably with Cocamidopropyl betaine and/or Lauroapho(di)acetate in order to increase their gentleness.

In a second preferred embodiment, preferred hair cleansing products as contemplated herein are those that, as anionic surfactant a), contain at least one alkyl(ether) sulfate salt of general formula $R-(OCH_2CH_2)_n-OSO_3X$, in which R means a straight-chain or branched, saturated or unsaturated alkyl group having from 8 to 24 C atoms, n means the number 0 or from about 1 to about 12, and X means an alkali, alkaline earth, ammonium, or alkanolamine ion.

For some fields of application, for example for the cleansing and nourishing of heavily damaged hair and/or particularly fine hair and/or baby or child's hair, it can be advantageous to dispense entirely with the use of sulfate surfactants.

An omission of sulfate surfactants, however, is often accompanied by a dramatic worsening of the foaming properties (quantity and quality), and therefore the selection of suitable surfactants is very arduous. The incorporation of oil-based care substances into hair cleansing products additionally has a negative effect on the stability, the viscosity and the foaming properties of the products. It has been found that nourishing hair cleansing products having good foaming properties and excellent nourishing potential can be produced when at least one surfactant from the group of anionic sarcosinate surfactants and/or taurate surfactants and/or isethionate surfactants and/or sulfosuccinate surfactants and/or alpha-olefin sulfonate surfactants is selected as anionic, sulfate-free surfactant base a). At least one of these surfactants is preferably combined with Cocamidopropyl betaine and/or Lauroapho(di)acetate as surfactant type b).

In a third preferred embodiment, preferred hair cleansing products as contemplated herein are those that are free from anionic sulfate surfactants and that, as anionic surfactant a), contain at least one surfactant from the group of anionic sarcosinate surfactants and/or taurate surfactants and/or isethionate surfactants and/or sulfosuccinate surfactants and/or alpha-olefin sulfonate surfactants.

The one or more anionic surfactants a) is (are) used in the hair cleansing products as contemplated herein (in relation to the total weight thereof) preferably in an amount of from about 3.00 to about 30.00% by weight, more preferably from about 4.00 to about 25.00% by weight, particularly preferably from about 4.50 to about 20.00% by weight and in particular from about 5.00 to about 15.00% by weight.

The one or more amphoteric surfactant(s) is (are) used in the hair cleansing products as contemplated herein (in relation to the total weight thereof) preferably in an amount of from about 1.00 to about 20.00% by weight, more preferably from about 1.25 to about 17.50% by weight, particularly preferably from about 1.50 to about 15.00% by weight and in particular from about 2.00 to about 10.00% by weight.

As further essential constituent, the hair cleansing products as contemplated herein contain a mixture of specific linear alkanes c) and d).

These can be incorporated without difficulty into compositions having a proportion of anionic and amphoteric surfactants a) and b) in the presence of non-polymeric structuring agents e).

The resultant hair-cleansing products, after rinsing, do not leave behind an oily, heavy feel, as can sometimes be observed after use (in particular regular use) of silicone-containing hair cleansing products (what is known as a build-up effect). Instead, the sensory properties and the combability and/or detangling capability of the hair after the use of the products could be significantly improved.

The use of linear alkanes c) that contain at least about 50% by weight $C_{12}$ alkane (dodecanes) has proven to be particularly advantageous for the cosmetic effect.

The use of linear alkanes d) that contain at least about 50% by weight $C_{22}$ alkane (docosanes) has also proven to be particularly advantageous for the cosmetic effect.

The use of
linear alkanes c) known under the INCI name Dodecanes and
linear alkanes d) known under the INCI name Docosanes
has proven to be in particular advantageous for the cosmetic effect.

Corresponding hair cleansing products are exemplified in a further preferred embodiment in that they contain at least about 50% by weight $C_{12}$ alkanes (Dodecanes) and at least about 50% by weight $C_{22}$ alkanes (Docosanes).

In a fourth preferred embodiment the hair cleansing products as contemplated herein contain
at least one linear alkane c) known under the INCI name Dodecane and
at least one linear alkane d) known under the INCI name Docosane.

The linear alkanes c) and d) are preferably obtainable exclusively from plant sources, for example in accordance with a method described in document US 2008/0287722.

Alternatively, commercially available alkanes c) and d) can also be used in the hair cleansing products as contemplated herein, for example the substances available under the trade names Parafol® 12-97 (INCI name: Dodecane) and Parafol® 22-95 (INCI name: Docosane).

The linear alkanes c) and d) are used in the hair cleansing products as contemplated herein preferably in a proportion by weight of, in each case, from about 0.10 to about 20.00% by weight (more preferably from about 0.15 to about 17.00% by weight, particularly preferably from about 0.20 to about 15.00% by weight, and in particular from about 0.25 to about 10.00% by weight), in the total weight of the hair cleansing products.

Preferably, from about 0.10 to about 20.00% by weight Dodecane and from about 0.1 to about 20% by weight Docosane are used in the hair cleansing products as contemplated herein.

The use of linear alkanes c) and d)—in particular of Dodecane and Docosane—in a ratio by weight c): d) of from about 9:1 to about 1:1, more preferably of from about 7:1 to about 1:1, particularly preferably of from about 5:1 to about 1:1 and in particular of from about 3:1 to about 1:1 has proven to be particularly advantageous for the cosmetic effect.

A content of non-polymeric structuring agents e) in the hair cleansing products as contemplated herein is essential in order to suspend the care substances c) and d) and thus attain storage and viscosity stability of the compositions under fluctuating temperatures.

Suitable non-polymeric structuring agents e) in the sense of the present disclosure are preferably crystalline, hydroxyl-group-containing glycerides, such as trihydroxystearin, hydrogenated oils and/or modifications thereof.

These form, in the compositions as contemplated herein, a network that prevents coalescence and/or phase separation of constituents in the composition that are not soluble in one another.

Examples of particularly suitable crystalline, hydroxyl-group-containing structuring agents are, in the sense of the present disclosure, above all plant-based hydrogenated wax, such as hydrogenated (hardened) jojoba oil and/or hydrogenated (hardened) castor oil.

The compound commercially available from a number of suppliers for example under the trade names Cutina® HR, Thixin® or Castorwax® and known under the INCI name Hydrogenated Castor Oil is very particularly preferred.

In a fifth preferred embodiment, the hair cleansing products as contemplated herein contain, as non-polymeric structuring agent e), a crystalline hydroxyl-group-containing glyceride, preferably hardened castor oil.

Within this embodiment, it is advantageous in particular if the hair-cleansing products as contemplated herein contain, as non-polymeric structuring agent e), a compound known under the INCI name Hydrogenated Castor Oil.

The one or more non-polymeric structuring agent(s) e) is (are) used in the hair cleansing products as contemplated herein (in relation to the total weight thereof) preferably in an amount of from about 0.01 to about 5.00% by weight, more preferably from about 0.02 to about 4.50% by weight, even more preferably from about 0.03 to about 4.00% by weight, particularly preferably from about 0.04 to about 3.50% by weight, and in particular from about 0.05 to about 3.00% by weight.

The nourishing properties of the hair cleansing products as contemplated herein can be even further increased if at least one cationic nourishing polymer f) is added to said products. Cationic nourishing polymers support the deposition of the alkanes c) and d) on the hairs, whereby the sensory properties of the hair can be improved, in particular by attaining a soft, silky feel of the hair.

In a further preferred embodiment, hair cleansing products as contemplated herein consequently contain at least one cationic polymer f) in a proportion by weight of from about 0.05 to about 5.00% by weight in the total weight of the hair cleansing product.

Particularly preferably, from about 0.10 to about 3.00% by weight, and in particular from about 0.15 to about 2.00% by weight of one or more cationic polymers f) are used in the hair cleansing products as contemplated herein.

Suitable cationic nourishing polymers f) are to be understood to mean, for example:

quaternised cellulose polymers, particularly Polyquaternium-10, as are commercially available under the names Celquat® and Polymer JR®, hydrophobically modified cellulose derivatives, for example the cationic polymers sold under the trade name SoftCat®, cationic alkyl polyglycosides, cationised honey, for example the commercial product Honeyquat® 50, cationic guar derivatives, such as in particular the products sold under the trade names Cosmedia® Guar N-Hance® and Jaguar®, polymeric dimethyl diallyl ammonium salts and copolymers thereof with esters and amides of acrylic acid and methacrylic acid, particularly Polyquaternium-6 and Polyquaternium-7. The products commercially available under the names Merquat® 100 (poly(dimethyl diallyl ammonium chloride)) and Merquat® 550 (dimethyl diallyl ammonium chloride-acrylamide copolymer) are examples of such cationic polymers, copolymers of vinylpyrrolidone with quaternised derivatives of dialkylamino alkyl acrylate and methacrylate, such as vinylpyrrolidone-dimethylaminoethyl methacrylate copolymers quaternised with diethyl sulfate. Such compounds are commercially available under the names Gafquat® 734 and Gafquat® 755, vinylpyrrolidone-vinylimidazolium methochloride copolymers, as are sold under the names Luviquat® FC 370, FC 550, FC 905 and HM 552, quaternised polyvinyl alcohol, and the polymers known under the names Polyquaternium 2, Polyquaternium 17, Polyquaternium 18, Polyquaternium-24, Polyquaternium 27, Polyquaternium-32, Polyquaternium-37, Polyquaternium 74 and Polyquaternium 89

Particularly preferred cationic polymers f) are quaternised cellulose polymers, hydrophobically modified quaternised cellulose polymers, cationic guar derivatives and/or cationic polymers based on acrylic acid (derivative), which are particularly preferably selected from the polymers known under the INCI names Guar Hydroxypropyltrimonium Chloride, Polyquaternium-6, Polyquaternium-7, Polyquaternium-10, Polyquaternium-37 and/or Polyquaternium-67.

In the sense of the present disclosure, cationic polysaccharide polymers, particularly Guar Hydroxypropyltrimonium Chloride, are preferred in particular.

Particularly good stability and particularly good hair nourishing results (in particular in respect of the sensory properties such as softness, silkiness, and smoothness) can be attained when the hair cleansing products as contemplated herein, besides the previously mentioned linear alkanes c) and d), do not contain any other fat phase constituents, in particular no silicone oils.

In a further preferred embodiment, hair cleansing products as contemplated herein are therefore substantially free of silicones.

The term "substantially free" is understood to mean that the hair treatment products as contemplated herein preferably contain less than about 0.1% by weight, more preferably less than about 0.05% by weight, and in particular no silicones (in relation to the total weight of the hair cleansing products).

Here, the amounts specified before both for freely added silicone and for silicones that can be contained as appropriate as secondary product in trade products are applicable.

in order to further improve the cosmetic properties of the products as contemplated herein, it can be advantageous if the hair cleansing products, in relation to their weight, additionally contain from about 0.10 to about 3.00% by weight, preferably from about 0.20 to about 2.50% by weight, particularly preferably from about 0.30 to about 2.00% by weight, and in particular from about 0.40 to about 1.50% by weight of at least one non-ionic surfactant g).

Suitable non-ionic surfactants g) are, for example
  addition products of from about 4 to about 30 mol ethylene oxide and/or from about 0 to about 5 mol propylene oxide with linear fatty alcohols having from 8 to 22 C atoms, with fatty acids having from 12 to 22 C atoms, and with alkyl phenols having from 8 to 15 C atoms in the alkyl group,
  ethylene oxide and polyglycerol addition products with methylglucoside fatty acid esters, fatty acid alkanolamides, and fatty acid glucamides,
  $C_8$-$C_{30}$ fatty acid mono- and diesters of addition products of from about 1 to about 30 mol ethylene oxide with glycerol,
  amine oxides,
  sorbitol fatty acid esters and addition products of ethylene oxide with sorbitol fatty acid esters, such as polysorbates,
  fatty acid alkanolamides of the following general formula,

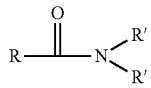

in which R preferably means a linear or branched, saturated or unsaturated alkyl or alkenyl group having from 8 to 24 carbon atoms, and the groups R' stand for hydrogen or for the group —$(CH_2)_n$OH, in which n means the numbers from about 2 or about 3, with the provision that at least one of the groups R' stands for the aforementioned group —$(CH_2)_n$OH,
  sugar fatty acid esters and addition products of ethylene oxide with sugar fatty acid esters, addition products of ethylene oxide with fatty acid alkanolamides and fatty amines and/or alkyl(oligo)glucosides,
    mixtures of alkyl(oligo)glucosides and fatty alcohols, for example the commercially available product Montanov®68,
    addition products of from about 5 to about 60 mol ethylene oxide with castor oil and hardened castor oil,
    partial esters of polyols with from 3 to 6 carbon atoms with saturated fatty acids having from 8 to 22 C atoms,
    sterols. Sterols are understood to mean a group of steroids which carry a hydroxyl group on C atom 3 of the steroid backbone and are isolated both from animal tissue (zoosterols) and from plant fats (phytosterols). Examples of zoosterols are cholesterol and lanosterol. Examples of suitable phytosterols are ergosterol, stigmasterol, and sitosterol. Sterols are also isolated from fungi and yeasts and are known in this case as mycosterols.
    phospholipids. These include, in particular, the glucose phospholipids, which are obtained for example as lecithins or phosphatidylcholines from, for example, egg yolk or plant seeds (for example soybeans).

Suitable alkyl (oligo)glycosides can be selected from compounds of the general formula RO-$[G]_x$, in which [G] preferably derives from aldoses and/or ketoses having from 5 to 6 carbon atoms, preferably from glucose.

The index number x stands for the degree of oligomerisation (DP), i.e. for the distribution of the mono- and oligoglycosides. The index number x preferably has a value in the range from about 1 to about 10, particularly preferably in the range from about 1 to about 3, wherein it is not necessarily an integer, but can be a fractional number, which can be determined analytically.

Particularly preferred alkyl (oligo)glycosides have a degree of oligomerisation between from about 1.2 and about 1.5.

The group R preferably stands for at least one alkyl and/or alkenyl group having from 4 to 24 C atoms.

Particularly preferred alkyl (oligo)glycosides are the compounds known by the INCI names Caprylyl/Capryl Glucoside, Decyl Glucoside, Lauryl Glucoside and Coco Glucoside.

Suitable amine oxides can be selected from at least one compound of general formulas (I) or (II)

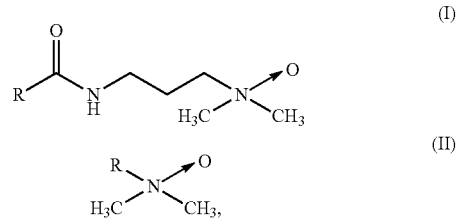

in which R stands in each case for a straight-chained or branched, saturated or mono- or polyunsaturated alkyl or alkenyl group having from 6 to 24 carbon atoms, preferably having from 8 to 18 carbon atoms.

The surfactants of the above-mentioned formulas (I) or (II) known by the INCI names Cocamine Oxide, Lauramine Oxide and/or Cocamidopropylamine Oxide and commercially available from various providers are particularly preferred.

Suitable $C_8$-$C_{30}$ fatty acid mono- and di-esters of addition products of from about 1 to about 30 mol ethylene oxide with glycerol are preferably understood to be those that are known by the INCI names PEG(1-10) Glyceryl Cocoate, in particular PEG-7 Glyceryl Cocoate.

It can also be advantageous to combine the ethoxylated fatty acid esters with further ethoxylated fatty acid esters. Such product mixtures are commercially available—for example under the name "Antil 200®" (INCI name: PEG-200 Hydrogenated Glyceryl Palmate, PEG-7 Glyceryl Cocoate) from the company Evonik.

Particularly preferred non-ionic surfactants g) that can be contained in the compositions as contemplated herein are fatty acid alkanolamides, alkyl(oligo)glucosides and $C_8$-$C_{30}$ fatty acid mono- and diesters of addition products of from about 1 to about 30 mol ethylene oxide with glycerol.

Cocamide MEA and/or PEG-7 Glyceryl Cocoate are preferred in particular on account of their foam-stabilising and hydrating properties.

Besides the aforementioned essential and optional constituents a) to g) the hair cleansing products as contemplated herein, in a further preferred embodiment for further increasing the nourishing properties of the products, can contain at least one further hair-conditioning active substance, which can be selected from the group of
protein hydrolysates and/or
vitamins.

Suitable protein hydrolysates are to be understood to be product mixtures that can be obtained by acid-, base- or enzyme-catalysed degradation of proteins. Protein hydrolysates of plant, animal and/or marine origin can be used.

Animal protein hydrolysates are, for example, elastin, collagen, keratin, silk and milk protein hydrolysates, which can also be present in the form of salts. Such products are marketed for example under the trade names Dehylan® (Cognis), Promois® (Interorgana) Collapuron® (Cognis), Nutrilan® (Cognis), Gelita-Sol® (German gelatin factories Stoess & Co), Lexein® (Inolex) and Kerasol® (Croda).

Protein hydrolysates of plant origin are preferred, for example soy, almond, rice, pea, potato and wheat protein hydrolysates. Such products are obtainable, for example, under the trade names Gluadin® (Cognis), DiaMin® (Diamalt), Lexein® (Inolex) and Crotein® (Croda).

Cationised protein hydrolysates can be also used, wherein the basic protein hydrolysate can originate from animals, for example, from collagen, milk or keratin, from plants, for example, from wheat, maize, rice, potatoes, soya or almonds, from marine life, for example, from fish collagen or algae, or from biotechnologically obtained protein hydrolysates. The protein hydrolysates forming the basis of the cationic derivatives can be obtained from the corresponding proteins by a chemical hydrolysis, particularly alkaline or acid hydrolysis, by an enzymatic hydrolysis and/or a combination of both types of hydrolysis. The hydrolysis of proteins generally produces a protein hydrolysate with a molecular weight distribution from about 100 daltons up to several thousand daltons. Cationic protein hydrolysates that are preferred are those of which the base protein content has a molecular weight of from about 100 to about 25.000 daltons, preferably from about 250 to about 5.000 daltons. Moreover, cationic protein hydrolysates are understood to include quaternised amino acids and their mixtures. Quaternisation of the protein hydrolysates or the amino acids is often carried out using quaternary ammonium salts such as, for example, N,N-dimethyl-N-(n-alkyl)-N-(2-hydroxy-3-chloro-n-propyl) ammonium halides. Moreover, the cationic protein hydrolysates can also be further derivatised. Typical examples of cationic protein hydrolysates and derivatives are the commercially available products known under the INCI names: Cocodimonium Hydroxypropyl Hydrolyzed Collagen, Cocodimopnium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropylt-rimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hy droxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quatemium-79 Hydrolyzed Keratin, Quatemium-79 Hydrolyzed Milk Protein, Quaternium-79 Hydrolyzed Silk, Quaternium-79 Hydrolyzed Soy Protein, Quaternium-79 Hydrolyzed Wheat Protein.

The proportion by weight of the one or more protein hydrolysate(s) in the total weight of the hair cleansing product is preferably from about 0.01 to about 5% by weight, more preferably from about 0.025 to about 3% by weight, and in particular from about 0.05 to about 2% by weight.

Suitable vitamins are preferably understood to mean the following vitamins, provitamins and vitamin precursors and derivatives thereof:

Vitamin A: the group of substances referred to as vitamin A includes retinol (Vitamin $A_1$) and 3,4-didehydroretinol (Vitamin $A_2$). β-carotene is the provitamin of retinol. Examples of suitable vitamin A components include vitamin A acid and esters thereof, vitamin A aldehyde, and vitamin A alcohol as well as esters thereof, such as the palmitate and acetate.

Vitamin B: the vitamin B group or the vitamin B complex includes, inter alia,
Vitamin $B_1$ (thiamine)
Vitamin $B_2$ (riboflavin)
Vitamin $B_3$. This often includes the compounds of nicotinic acid and nicotinic acid amide (niacinamide.
Vitamin $B_5$ (pantothenic acid and panthenol). In the context of this group, panthenol is preferably used. Useable derivatives of panthenol are especially the esters and ethers of panthenol, pantolactone, and also cationically derivatised panthenols. Specific representatives are, for example, panthenol triacetate, panthenol monoethyl ether and monoacetate thereof, as well as cationic panthenol derivatives.
Vitamin $B_6$ (pyridoxine and also pyridoxamine and pyridoxal).

Vitamin C (ascorbic acid): the use in the form of the palmitic acid ester, the glucosides, or phosphates can be preferred. The use in combination with tocopherols can also be preferred.

Vitamin E (tocopherols, in particular α-tocopherol).

Vitamin F: the term "vitamin F" is usually understood to mean essential fatty acids, in particular linoleic acid, linolenic acid and arachidonic acid.

Vitamin H: The compound (3 aS,4S,6aR)-2-oxohexahydrothienol[3,4-d]-imidazol-4-valeric acid denotes vitamin H, for which the trivial name however (biotin) has become accepted.

Vitamins, provitamins and vitamin precursors from the groups A, B, E and H are particularly preferred. Nicotinic acid amide, biotin, pantolactone and/or panthenol are preferred in particular. The proportion by weight of the vitamin(s), vitamin derivative(s), and/or the vitamin precursor(s) in the total weight of the hair cleansing product is preferably from about 0.001 to about 2% by weight, particularly preferably from about 0.005 to about 1% by weight, and in particular from about 0.01 to about 0.5% by weight.

It has been found that the hair cleansing products as contemplated herein are also suitable for use as an anti-dandruff preparation.

The total weight of anti-dandruff agents in the total weight of the hair cleansing products can preferably be from about 0.01 to about 10% by weight, more preferably from about 0.025 to about 7.5% by weight, particularly preferably from about 0.05 to about 5% by weight, and in particular from about 0.075 to about 3% by weight.

Suitable anti-dandruff active substances can be selected from piroctone olamines, climbazole, zinc pyrithione, ketoconazoles, salicylic acid, sulfur, selenium sulfide, tea preparations, undecenoic acid derivatives, burdock extracts, poplar extracts, stinging nettle extracts, walnut shell extracts, birch extracts, willow bark extracts, rosemary extracts and/or arnica extracts.

Climbazole, zinc pyrithione, and piroctone olamines are preferred. Zinc pyrithione is preferred in particular.

Further active substances, auxiliaries and additives that can be contained with preference in the hair cleansing products as contemplated herein are, for example:

plant extracts,
humectants,
fragrances,
UV filters,
thickening agents such as gelatins or plant gums, for example agar-agar, guar gum, alginates, xanthan gum, gum arabic, karaya gum, locust bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays and sheet silicates, such as bentonite or fully synthetic hydrocolloids such as polyvinyl alcohol, the Ca, Mg or Zn soaps,
structurants, such as maleic acid and lactic acid,
dimethyl isosorbide,
cyclodextrins,
fibre structure-improving active substances, in particular mono-, di- and oligosaccharides, such as glucose, galactose, fructose, fruit sugar, and lactose,
dyes for coloring the product,
substances for adjusting the pH value, for example α- and β-hydroxy carboxylic acids, such as citric acid, lactic acid, malic acid, glycolic acid,
active substances such as bisabolol and/or allantoin,
complexing agents, such as EDTA, NTA, β-alanine diacetic acid and phosphonic acids,
ceramides. Ceramides are understood to mean N-acyl-sphingosine (fatty acid amides of sphingosine) or synthetic analogues such as lipids (what are known as pseudo ceramides),
propellants, such as propane-butane mixtures, $N_2O$, dimethylether, $CO_2$ and air,
antioxidants,
preservatives, such as sodium benzoate or salicylic acid,
additional viscosity regulators, such as salts (NaCl).

A second subject of the present disclosure is cosmetic use of the hair cleansing product as contemplated herein for the cleansing and nourishing of hair, in particular in order to improve the wet and dry combability,
the detangling capability,
the feel, and
the shine of hair.

That stated with regard to the products as contemplated herein applies, mutatis mutandis, in respect of further preferred embodiments of the use as contemplated herein.

The following examples shall explain the subject of the present disclosure, but without limiting it.

EXAMPLES a) The following hair cleansing compositions as contemplated herein were produced (the specified amounts relate to % by weight):

|  | 1 | 2 | 3 | 4 |
|---|---|---|---|---|
| Anionic surfactant | 3.00-30.00 | 4.00-25.00 | 4.50-20.00 | 5.00-15.00 |
| Amphoteric surfactant | 1.00-20.00 | 1.25-17.50 | 1.50-15.00 | 2.00-10.00 |
| linear $C_9$, $C_{10}$, $C_{11}$ and/or $C_{12}$ alkane | 0.10-20.00 | 0.15-17.00 | 0.20-15.00 | 0.25-10.00 |
| linear $C_{15}$, $C_{16}$, $C_{17}$, $C_{18}$, $C_{19}$, $C_{20}$, $C_{21}$, $C_{22}$ and/or $C_{23}$ alkane | 0.10-20.00 | 0.15-17.00 | 0.20-15.00 | 0.25-10.00 |
| Non-polymeric structuring agent | 0.01-5.00 | 0.02-4.50 | 0.03-4.00 | 0.05-3.00 |
| Water and optionally further auxiliaries and additives | to 100 | to 100 | to 100 | to 100 |

|  | 5 | 6 | 7 | 8 |
|---|---|---|---|---|
| Alkyl(ether)sulfate or taurate surfactant and alpha-olefinsulfonate surfactant | 3.00-30.00 | 4.00-25.00 | 4.50-20.00 | 5.00-15.00 |
| Amphoteric surfactant | 1.00-20.00 | 1.25-17.50 | 1.50-15.00 | 2.00-10.00 |
| linear $C_9$, $C_{10}$, $C_{11}$ and/or $C_{12}$ alkane | 0.10-20.00 | 0.15-17.00 | 0.20-15.00 | 0.25-10.00 |
| linear $C_{15}$, $C_{16}$, $C_{17}$, $C_{18}$, $C_{19}$, $C_{20}$, $C_{21}$, $C_{22}$ and/or $C_{23}$ alkane | 0.10-20.00 | 0.15-17.00 | 0.20-15.00 | 0.25-10.00 |
| Non-polymeric structuring agent | 0.01-5.00 | 0.02-4.50 | 0.03-4.00 | 0.05-3.00 |

| | | | | |
|---|---|---|---|---|
| Water and optionally further auxiliaries and additives | to 100 | to 100 | to 100 | to 100 |

| | 9 | 10 | 11 | 12 |
|---|---|---|---|---|
| Anionic surfactant | 3.00-30.00 | 4.00-25.00 | 4.50-20.00 | 5.00-15.00 |
| Cocamidopropyl betaine and/or Disodium Cocoampho(di)acetate | 1.00-20.00 | 1.25-17.50 | 1.50-15.00 | 2.00-10.00 |
| linear $C_9$, $C_{10}$, $C_{11}$ and/or $C_{12}$ alkane | 0.10-20.00 | 0.15-17.00 | 0.20-15.00 | 0.25-10.00 |
| linear $C_{15}$, $C_{16}$, $C_{17}$, $C_{18}$, $C_{19}$, $C_{20}$, $C_{21}$, $C_{22}$ and/or $C_{23}$ alkane | 0.10-20.00 | 0.15-17.00 | 0.20-15.00 | 0.25-10.00 |
| Non-polymeric structuring agent | 0.01-5.00 | 0.02-4.50 | 0.03-4.00 | 0.05-3.00 |
| Water and optionally further auxiliaries and additives | to 100 | to 100 | to 100 | to 100 |

| | 13 | 14 | 15 | 16 |
|---|---|---|---|---|
| Anionic surfactant | 3.00-30.00 | 4.00-25.00 | 4.50-20.00 | 5.00-15.00 |
| Amphoteric surfactant | 1.00-20.00 | 1.25-17.50 | 1.50-15.00 | 2.00-10.00 |
| Dodecane | 0.10-20.00 | 0.15-17.00 | 0.20-15.00 | 0.25-10.00 |
| linear $C_{15}$, $C_{16}$, $C_{17}$, $C_{18}$, $C_{19}$, $C_{20}$, $C_{21}$, $C_{22}$ and/or $C_{23}$ alkane | 0.10-20.00 | 0.15-17.00 | 0.20-15.00 | 0.25-10.00 |
| Non-polymeric structuring agent | 0.01-5.00 | 0.02-4.50 | 0.03-4.00 | 0.05-3.00 |
| Water and optionally further auxiliaries and additives | to 100 | to 100 | to 100 | to 100 |

| | 17 | 18 | 19 | 20 |
|---|---|---|---|---|
| Anionic surfactant | 3.00-30.00 | 4.00-25.00 | 4.50-20.00 | 5.00-15.00 |
| Amphoteric surfactant | 1.00-20.00 | 1.25-17.50 | 1.50-15.00 | 2.00-10.00 |
| Dodecane | 0.10-20.00 | 0.15-17.00 | 0.20-15.00 | 0.25-10.00 |
| Docosane | 0.10-20.00 | 0.15-17.00 | 0.20-15.00 | 0.25-10.00 |
| Non-polymeric structuring agent | 0.01-5.00 | 0.02-4.50 | 0.03-4.00 | 0.05-3.00 |
| Water and optionally further auxiliaries and additives | to 100 | to 100 | to 100 | to 100 |

| | 21 | 22 | 23 | 24 |
|---|---|---|---|---|
| Anionic surfactant | 3.00-30.00 | 4.00-25.00 | 4.50-20.00 | 5.00-15.00 |
| Amphoteric surfactant | 1.00-20.00 | 1.25-17.50 | 1.50-15.00 | 2.00-10.00 |
| linear $C_9$, $C_{10}$, $C_{11}$ and/or $C_{12}$ alkane | 0.10-20.00 | 0.15-17.00 | 0.20-15.00 | 0.25-10.00 |
| linear $C_{15}$, $C_{16}$, $C_{17}$, $C_{18}$, $C_{19}$, $C_{20}$, $C_{21}$, $C_{22}$ and/or $C_{23}$ alkane | 0.10-20.00 | 0.15-17.00 | 0.20-15.00 | 0.25-10.00 |
| Hydrogenated Castor Oil | 0.01-5.00 | 0.02-4.50 | 0.03-4.00 | 0.05-3.00 |
| Water and optionally further auxiliaries and additives | to 100 | to 100 | to 100 | to 100 |

| | 25 | 26 | 27 | 28 |
|---|---|---|---|---|
| Alkyl(ether)sulfate or taurate surfactant and alpha-olefinsulfonate surfactant | 3.00-30.00 | 4.00-25.00 | 4.50-20.00 | 5.00-15.00 |
| Cocamidopropyl betaine and/or Disodium Cocoampho(di)acetate | 1.00-20.00 | 1.25-17.50 | 1.50-15.00 | 2.00-10.00 |
| linear $C_9$, $C_{10}$, $C_{11}$ and/or $C_{12}$ alkane | 0.10-20.00 | 0.15-17.00 | 0.20-15.00 | 0.25-10.00 |
| linear $C_{15}$, $C_{16}$, $C_{17}$, $C_{18}$, $C_{19}$, $C_{20}$, $C_{21}$, $C_{22}$ and/or $C_{23}$ alkane | 0.10-20.00 | 0.15-17.00 | 0.20-15.00 | 0.25-10.00 |
| Non-polymeric structuring agent | 0.01-5.00 | 0.02-4.50 | 0.03-4.00 | 0.05-3.00 |
| Water and optionally further auxiliaries and additives | to 100 | to 100 | to 100 | to 100 |

| | 29 | 30 | 31 | 32 |
|---|---|---|---|---|
| Alkyl(ether)sulfate or taurate surfactant and alpha-olefinsulfonate surfactant | 3.00-30.00 | 4.00-25.00 | 4.50-20.00 | 5.00-15.00 |
| Cocamidopropyl betaine and/or Disodium Cocoampho(di)acetate | 1.00-20.00 | 1.25-17.50 | 1.50-15.00 | 2.00-10.00 |
| Dodecane | 0.10-20.00 | 0.15-17.00 | 0.20-15.00 | 0.25-10.00 |

|  | | | | |
|---|---|---|---|---|
| Docosane | 0.10-20.00 | 0.15-17.00 | 0.20-15.00 | 0.25-10.00 |
| Non-polymeric structuring agent | 0.01-5.00 | 0.02-4.50 | 0.03-4.00 | 0.05-3.00 |
| Water and optionally further auxiliaries and additives | to 100 | to 100 | to 100 | to 100 |

|  | 33 | 34 | 35 | 36 |
|---|---|---|---|---|
| Alkyl(ether)sulfate or taurate surfactant and alpha-olefinsulfonate surfactant | 3.00-30.00 | 4.00-25.00 | 4.50-20.00 | 5.00-15.00 |
| Cocamidopropyl betaine and/or Disodium Cocoampho(di)acetate | 1.00-20.00 | 1.25-17.50 | 1.50-15.00 | 2.00-10.00 |
| Dodecane | 0.10-20.00 | 0.15-17.00 | 0.20-15.00 | 0.25-10.00 |
| Docosane | 0.10-20.00 | 0.15-17.00 | 0.20-15.00 | 0.25-10.00 |
| Hydrogenated Castor Oil | 0.01-5.00 | 0.02-4.50 | 0.03-4.00 | 0.05-3.00 |
| Water and optionally further auxiliaries and additives | to 100 | to 100 | to 100 | to 100 |

|  | 37 | 38 | 39 | 40 |
|---|---|---|---|---|
| Anionic surfactant | 3.00-30.00 | 4.00-25.00 | 4.50-20.00 | 5.00-15.00 |
| Amphoteric surfactant | 1.00-20.00 | 1.25-17.50 | 1.50-15.00 | 2.00-10.00 |
| linear $C_9$, $C_{10}$, $C_{11}$- and/or $C_{12}$ alkane | 0.10-20.00 | 0.15-17.00 | 0.20-15.00 | 0.25-10.00 |
| linear $C_{15}$, $C_{16}$, $C_{17}$, $C_{18}$, $C_{19}$, $C_{20}$, $C_{21}$, $C_{22}$- and/or $C_{23}$ alkane | 0.10-20.00 | 0.15-17.00 | 0.20-15.00 | 0.25-10.00 |
| Non-polymeric structuring agent | 0.01-5.00 | 0.02-4.50 | 0.03-4.00 | 0.05-3.00 |
| Cationic polymer | 0.05-5.00 | 0.10-3.00 | 0.15-2.00 | 0.20-1.00 |
| Water and optionally further auxiliaries and additives | to 100 | to 100 | to 100 | to 100 |

|  | 41 | 42 | 43 | 44 |
|---|---|---|---|---|
| Anionic surfactant | 3.00-30.00 | 4.00-25.00 | 4.50-20.00 | 5.00-15.00 |
| Amphoteric surfactant | 1.00-20.00 | 1.25-17.50 | 1.50-15.00 | 2.00-10.00 |
| linear $C_9$, $C_{10}$, $C_{11}$ and/or $C_{12}$ alkane | 0.10-20.00 | 0.15-17.00 | 0.20-15.00 | 0.25-10.00 |
| linear $C_{15}$, $C_{16}$, $C_{17}$, $C_{18}$, $C_{19}$, $C_{20}$, $C_{21}$, $C_{22}$ and/or $C_{23}$ alkane | 0.10-20.00 | 0.15-17.00 | 0.20-15.00 | 0.25-10.00 |
| Non-polymeric structuring agent | 0.01-5.00 | 0.02-4.50 | 0.03-4.00 | 0.05-3.00 |
| Cationic polymer | 0.05-5.00 | 0.10-3.00 | 0.15-2.00 | 0.20-1.00 |
| Non-ionic surfactant/non-ionic emulsifier | 0.10-3.00 | 0.20-2.50 | 0.30-2.00 | 0.40-1.50 |
| Water and optionally further auxiliaries and additives | to 100 | to 100 | to 100 | to 100 | b) Assessment of hair cleansing products as contemplated herein and comparative hair cleaning products not contemplated in this disclosure (i) Sulfate-free formulations

|  | 45 | 46 | 47 |
|---|---|---|---|
| Sodium Methyl Cocoyl Taurate | 5.80 | 5.80 | 5.80 |
| Sodium $C_{14-16}$ Olefin Sulfonate | 6.40 | 6.40 | 6.40 |
| Cocamidopropyl betaine | 3.00 | 3.00 | 3.00 |
| PEG-7 Glyceryl Cocoate | 0.20 | 0.20 | 0.20 |
| PEG-40 Hydrogenated Castor Oil | 0.30 | 0.30 | 0.30 |
| Polyglycerol fatty acid ester | 0.75 | 0.75 | 0.75 |
| Guar Hydroxypropyltrimonium Chloride | 0.20 | 0.20 | 0.20 |
| Xiameter MEM 1664 ®[1] |  | 0.50 |  |
| Dodecane (Parafol 12-97) |  |  | 0.35 |
| Docosane (Parafol 22-95) |  |  | 0.15 |
| Salicylic acid | 0.50 | 0.50 | 0.50 |
| 5% Hydrogenated Castor Oil Dispersion | 2.00 | 2.00 | 2.00 |
| Citric acid | 0.20 | 0.20 | 0.20 |
| Fragrance | 0.50 | 0.50 | 0.50 |
| NaCl | 0.15 | 0.15 | 0.15 |
| Water | to 100 | to 100 | to 100 |
| pH value | 5.0 ± 0.2 | 5.0 ± 0.2 | 5.0 ± 0.2 |
| Viscosity [mPas]* | 6.000-10.000 | 6.000-10.000 | 6.000-10.000 |
| Change (appearance) after 6 weeks storage at 45° C. | ok | ok | ok |
| Foam volume** | 1.7 | 2.0 | 2.0 |
| Foam quality** | 1.5 | 1.7 | 1.8 |
| Detangling capability (in wet hair)** | 2.3 | 2.1 | 1.9 |
| Combability (in wet hair)** | 2.7 | 2.3 | 2.5 |
| Feel (in wet hair)** | 2.4 | 2.0 | 2.1 |
| Detangling capability (in dry hair)** | 2.2 | 2.2 | 2.3 |
| Combability (in dry hair)** | 1.8 | 1.8 | 1.8 |
| Reduction in the wet combability [%] | 37 | 55 | 53 |

Composition 47 is as contemplated herein; compositions 45 and 46 are comparison compositions
(ii) Formulations with anionic sulfate surfactants

|  | 48 | 49 | 50 | 51 | 52 |
|---|---|---|---|---|---|
| Sodium Laureth Sulfate | 11.00 | 11.00 | 11.00 | 11.00 | 11.00 |
| Cocamidopropyl betaine | 2.50 | 2.50 | 2.50 | 2.50 | 2.50 |
| Disodium Cocoamphodiacetate | 1.50 | 1.50 | 1.50 | 1.50 | 1.50 |
| Guar Hydroxypropyltrimonium Chloride | 0.20 | 0.20 | 0.20 | 0.20 | 0.20 |
| PEG-12 Dimethicone | 0.50 | | | | |
| Amodimethicone | | 0.50 | | | |
| Dimethicone (50%; Microemulsion) | | | 1.00 | | |
| Dodecane (Parafol 12-97) | | | | 0.35 | |
| Docosane (Parafol 22-95) | | | | 0.15 | |
| PEG-40 Hydrogenated Castor Oil | 0.40 | 0.40 | 0.40 | 0.40 | 0.40 |
| Fragrance | 0.40 | 0.40 | 0.40 | 0.40 | 0.40 |
| Citric acid | 0.20-0.50 | 0.20-0.50 | 0.20-0.50 | 0.20-0.50 | 0.20-0.50 |
| NaCl | 1.00-1.50 | 1.00-1.50 | 1.00-1.50 | 1.00-1.50 | 1.00-1.50 |
| Euperlan PK 3000 AM ®[2] | 2.50 | 2.50 | 2.50 | 2.50 | 2.50 |
| 5% Hydrogenated Castor Oil Dispersion | 1.00 | 1.00 | 1.00 | 1.00 | 1.00 |
| Preservative (sodium benzoate + salicylic acid) | 0.50 | 0.50 | 0.50 | 0.50 | 0.50 |
| Water | to 100 | to 100 | to 100 | to 100 | to 100 |
| pH value ± 0.1 | 5.0 | 5.0 | 5.0 | 5.0 | 5.0 |
| Viscosity [mPas]* | 10.000 | 10.000 | 10.000 | 10.000 | 10.000 |
| Change (appearance) after 6 weeks storage at 45° C. | ok | ok | ok | ok | ok |
| Reduction in wet combability [%] | 39 | 51 | 57 | 61 | 32 |
| Increase in shine [%]** | 78 | 91 | 83 | 89 | 60 |

Composition 51 is as contemplated herein; compositions 48 to 50 and 52 are comparison compositions
® [1]INCI name: Dimethicone, Laureth-4, Laureth-23 (Silicone Emulsion); Dow Corning
® [2]INCI name: Aqua, Glycol Distearate, Glycerin, Laureth-4, Cocamidopropyl Betaine, Formic Acid
*measured with Brookfield at 20° C.; 20 rpm
**The specified value corresponds to the mean value of the absolute assessments of 10 experts, who awarded scores 1 to 5 (with 1 = very good; 5 = poor) in each of the categories While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A sulfate-free hair cleansing product that exhibits improved detangling capability and comprising
    a) at least one anionic surfactant comprising a taurate and present in an amount of from about 5 to about 15% by weight,
    b) at least one amphoteric surfactant comprising a betaine and present in an amount of from about 2 to about 10% by weight,
    c) dodecane present in an amount of from about 0.1 to about 20% by weight,
    d) docosane present in an amount of from about 0.1 to about 20% by weight, and
    e) at least one non-polymeric structuring agent comprising hydrogenated castor oil and present in an amount of from about 0.05 to about 3% by weight, wherein the cleaning product has a pH of 5.0±0.2, wherein
    the taurate is sodium methyl cocoyl taurate,
    the betaine is cocamidopropyl betaine, and
    the hydrogenated castor oil is a 5 wt % dispersion, and
wherein the sulfate-free hair cleansing product further comprises,
    sodium C14-16 olefin sulfonate,
    PEG-7 glyceryl cocoate,
    PEG-40 hydrogenated castor oil,
    polyglycerol fatty acid ester,
    guar hydroxypropyltrimonium chloride,
    salicylic acid,
    citric acid,
    fragrance,
    NaCl, and
    water that is present in an amount such that the total weight percent of all components sums to 100 wt %.

2. The sulfate-free hair cleansing product of claim 1 consisting of:
    said sodium methyl cocoyl taurate,
    said cocamidopropyl betaine,
    said dodecane,
    said docosane,
    said hydrogenated castor oil,
    said sodium C14-16 olefin sulfonate,
    said PEG-7 glyceryl cocoate,
    said PEG-40 hydrogenated castor oil,
    said polyglycerol fatty acid ester,
    said guar hydroxypropyltrimonium chloride,
    said salicylic acid,
    said citric acid,
    said fragrance, said NaCl, and
said water.

3. The sulfate-free hair cleansing product of claim 1 wherein
the sodium methyl cocoyl taurate is present in an amount of 5.80 wt %,
the cocamidopropyl betaine is present in an amount of 3.00 wt %,
the dodecane is present in an amount of 0.35 wt %,
the docosane is present in an amount of 0.15 wt %, and
the dispersion is present in an amount of 2.00 wt %,
the sodium C14-16 olefin sulfonate is present in an amount of 6.40 wt %,
the PEG-7 glyceryl cocoate is present in an amount of 0.20 wt %,
the PEG-40 hydrogenated castor oil is present in an amount of 0.30 wt %,
the polyglycerol fatty acid ester is present in an amount of 0.75 wt %,
the guar hydroxypropyltrimonium chloride is present in an amount of 0.20 wt %,
the salicylic acid is present in an amount of 0.50 wt %,
the citric acid is present in an amount of 0.20 wt %,
the fragrance is present in an amount of 0.50 wt %,
the NaCl is present in an amount of 0.15 wt %, and
the water is present in an amount such that the total weight percent of all components sums to 100 wt %.

4. The sulfate-free hair cleansing product of claim 3 consisting of:
said sodium methyl cocoyl taurate,
said cocamidopropyl betaine,
said dodecane,
said docosane,
said hydrogenated castor oil,
said sodium C14-16 olefin sulfonate,
said PEG-7 glyceryl cocoate,
said PEG-40 hydrogenated castor oil,
said polyglycerol fatty acid ester,
said guar hydroxypropyltrimonium chloride,
said salicylic acid,
said citric acid,
said fragrance,
said NaCl, and
said water.

5. A hair cleansing product that exhibits improved reduction in wet combability and comprises:
a) at least one anionic surfactant comprising a sulfate and present in an amount of from about 5 to about 15% by weight,
b) at least one amphoteric surfactant comprising a betaine and present in an amount of from about 2 to about 10% by weight,
c) dodecane present in an amount of from about 0.1 to about 20% by weight,
d) docosane present in an amount of from about 0.1 to about 20% by weight, and
e) at least one non-polymeric structuring agent comprising hydrogenated castor oil and present in an amount of from about 0.05 to about 3% by weight,
wherein the cleaning product has a pH of 5.0±0.1,
wherein
the sulfate is sodium laureth sulfate,
the betaine is cocamidopropyl betaine, and
the hydrogenated castor oil is a 5 wt % dispersion and is present in an amount of 1 wt %, and
wherein the hair cleansing product further comprises,
disodium cocoamphodiacetate,
guar hydroxypropyltrimonium chloride,
PEG-40 hydrogenated castor oil,
fragrance,
citric acid,
NaCl,
a component comprising water, glycol distearate, glycerin, laureth-4, cocamidopropyl betaine, and formic acid,
a preservative that is sodium benzoate and salicylic acid, and
water that is present in an amount such that the total weight percent of all components sums to 100 wt %.

6. The hair cleansing product of claim 5 consisting of
said sodium laureth sulfate,
said cocamidopropyl betaine,
said dodecane,
said docosane,
said hydrogenated castor oil,
said disodium cocoamphodiacetate,
said guar hydroxypropyltrimonium chloride,
said PEG-40 hydrogenated castor oil,
said fragrance,
said citric acid,
said NaCl,
said component comprising water, glycol distearate, glycerin, laureth-4, cocamidopropyl betaine, and formic acid,
said preservative that is sodium benzoate and salicylic acid, and
said water that is present in an amount such that the total weight percent of all components sums to 100 wt %.

7. The hair cleansing product of claim 5,
wherein
the sodium laureth sulfate is present in an amount of 11 wt %,
the cocamidopropyl betaine is present in an amount of 2.5 wt %,
the dodecane is present in an amount of 0.35 wt %,
the docosane is present in an amount of 0.15 wt %, and
the hydrogenated castor oil is present in an amount of 1 wt %,
the disodium cocoamphodiacetate is present in an amount of 1.50 wt %,
the guar hydroxypropyltrimonium chloride is present in an amount of 0.20 wt %,
the PEG-40 hydrogenated castor oil is present in an amount of 0.40 wt %,
the fragrance is present in an amount of 0.40 wt %,
the citric acid is present in an amount of 0.20-0.50 wt %,
the NaCl is present in an amount of 1.00-1.50 wt %,
the component comprising water, glycol distearate, glycerin, laureth-4, cocamidopropyl betaine, and formic acid is present in a total amount of 2.50 wt %,
the preservative that is sodium benzoate and salicylic acid is present in a total amount of 0.50 wt %, and
the water is present in an amount such that the total weight percent of all components sums to 100 wt %.

8. The hair cleansing product of claim 7 consisting of:
said sodium laureth sulfate,
said cocamidopropyl betaine,
said dodecane,
said docosane,
said hydrogenated castor oil,
said disodium cocoamphodiacetate,
said guar hydroxypropyltrimonium chloride,
said PEG-40 hydrogenated castor oil, said fragrance,
said citric acid,
said NaCl,
said component comprising water, glycol distearate, glycerin, laureth-4, cocamidopropyl betaine, and formic acid,
said preservative that is sodium benzoate and salicylic acid, and
said water.

* * * * *